US006770484B2

(12) United States Patent
Liang

(10) Patent No.: US 6,770,484 B2
(45) Date of Patent: Aug. 3, 2004

(54) USING FLAME AND GRAPHITE FURNACE ATOMIC ABSORPTION SPECTROMETRY FOR ANALYSIS OF SODIUM CHANNEL ACTIVITY

(76) Inventor: Dong C. Liang, 4882 Ontario St., Vancouver, British Columbia (CA), V5V 3H5

( * ) Notice: Subject to any disclaimer, the term of this patent is extended or adjusted under 35 U.S.C. 154(b) by 0 days.

(21) Appl. No.: 10/304,683

(22) Filed: Nov. 27, 2002

(65) Prior Publication Data

US 2003/0100121 A1 May 29, 2003

Related U.S. Application Data

(60) Provisional application No. 60/333,604, filed on Nov. 29, 2001.

(51) Int. Cl.$^7$ ............................................... G01N 33/48
(52) U.S. Cl. .............................. 436/63; 436/171; 435/4; 435/29; 356/300
(58) Field of Search .......................... 436/63, 171, 174, 436/173; 435/4, 29; 356/300, 317, 326

(56) References Cited

U.S. PATENT DOCUMENTS

| | | | | |
|---|---|---|---|---|
| 5,688,830 A | * | 11/1997 | Berger et al. ................ | 514/651 |
| 5,760,230 A | * | 6/1998 | Schohe-Loop et al. ..... | 544/284 |
| 5,858,687 A | | 1/1999 | Manger et al. | |
| 6,174,690 B1 | | 1/2001 | Manger et al. | |
| 6,355,413 B1 | | 3/2002 | Gage et al. | |
| 2002/0168625 A1 | * | 11/2002 | Weaver ......................... | 435/4 |
| 2003/0083249 A1 | * | 5/2003 | Brown et al. .................. | 514/12 |
| 2003/0176450 A1 | * | 9/2003 | Atkinson et al. ........ | 514/259.3 |

* cited by examiner

Primary Examiner—Maureen M. Wallenhorst

(57) ABSTRACT

A method of chemical analysis involving. Flame Atomic Absorption Spectroscopy (FAAS) and Graphite Furnace Atomic Absorption Spectroscopy (GFAAS) in combination with flux assays to directly measure intracellular ion concentration to analyze ion channel activity.

12 Claims, 1 Drawing Sheet

Figure 1. Protocol Summary

Plate Cells @ 50,000 to 100,000 cells/well —10

↓

18 Hours @ 37°C ——————— 20

↓

Wash 2X in Solution A (200 µL) ——— 30

↓

Incubate for 30 Seconds to 30 Minutes ——— 40
In Solution B (50 to 200 µL) @ 37°C

↓

Wash 3X in Solution A (200 µL) ——— 50

↓

Whole Cell Lysis ——————— 60
1.5% Triton-X 100

↙           ↘

FAAS         GFAAS       70

USING FLAME AND GRAPHITE FURNACE ATOMIC ABSORPTION SPECTROMETRY FOR ANALYSIS OF SODIUM CHANNEL ACTIVITY

RELATED APPLICATIONS

This application claims the benefit of prior filed provisional, Application No. 60/333,604 filed Nov. 29, 2001.

BACKGROUND OF THE INVENTION

An ion channel is a pore formed by one or more protein subunits in the cell membrane. This pore allows the diffusion of substances into (influx) and/or out of (efflux) the cell. These substances are usually ions or lipid-soluble molecules. Sodium channels are commonly found in nerve cells in the brain and spinal cord, and in skeletal muscle cells where sodium channel expression is high. Ion channels are distinct in many ways and have been characterized through advances in molecular biology and classified according to pharmacological and biophysical properties. Studies have revealed the selectivity of each class of ion channel, allowing certain ions to pass through. For example, potassium ions are very similar to sodium ions, but the potassium ions cannot pass through many sodium channels. Such distinguishing features are advantageous when developing methodologies to study these unique proteins.

Ion channels have many distinct biophysical functions. Sodium channels play a very important role in the propagation of action potentials in excitatory cells which function in such important processes as sensory perception. Disorders associated with abnormal sodium channel function include epilepsy and seizures, cardiac arrhythmias, mental illness, neuroma tumors (tumors derived from cells of the nervous system), various myotonias (types of myopathies with excessive muscle rigidity or contractions), hyper- and hypokalemic paralysis (types of myopathies with episodes of flaccid paralysis or weakness), hypothyroidism (under activity of the thyroid gland, which produces iodine hormones), various neuropathies (diseases of peripheral nerves, causing weakness or numbness), and allodynia and hyperaesthesia (both forms of hyper excitability, where sharp, shooting pain results from normally innocuous sensory stimuli, such as touch). Due to this wide range of disorders that are associated with sodium channels, pharmaceutical, medical, and biological research has focused their efforts to find drug candidates to treat and prevent sodium channel-related diseases.

Traditionally, analytical applications for ion channel analysis have fallen on either of the extremes of accuracy or speed. The patch-clamp method is indisputably the most accurate, but it has a low throughput speed. Fluorescent dye measurements offer unsurpassed analysis speed, but suffer from low accuracy. Furthermore, other techniques that manage to sit in the middle ground between high accuracy and fast speed do possess equally limited disadvantages. The radioactive $^{86}Rb^+$ efflux assay, for example, is a relatively unsafe and inconvenient technique in that the radioactive isotopes required are harmful to human operators, the half-life of the isotopes restricts the time duration of experiments, and there are radioactive waste disposal considerations to be dealt with. All of the techniques described above are an indirect measure of intracellular ion concentration. Accordingly it is an object of this invention to provide a method for preparing and analyzing sample cell cultures for ion channel activity such that a direct and accurate measurement of intracellular ion concentration may be achieved.

SUMMARY OF THE INVENTION

The present invention pertains to experimental methodologies for biopharmaceutical research, particularly for the analysis of drug candidates for therapeutic effects on ion channels. The invention describes a method of preparing sample cell cultures for analysis, and using a unique flux assay and the techniques of flame atomic absorption spectrometry (FAAS) or graphite furnace atomic absorption spectrometry (GFAAS) to directly measure the intracellular ion content of those cell cultures, enabling the measurement of ion flux and ion channel activity.

An advantage of this invention is that the experimental methodology described herein provides a way for researchers to accurately determine the therapeutic effects of candidate compounds for sodium channel drug discovery.

BRIEF DESCRIPTION OF DRAWINGS

Further features and advantages of the invention will be apparent from the following detailed description, given by way of example, of a preferred embodiment taken in conjunction with the accompanying drawings, wherein:

FIG. 1 is a block diagram of the procedure for preparing sample cell cultures.

DETAILED DESCRIPTION OF THE INVENTION

The first method of preparing the cell culture samples for analysis is called the Tracer Ion Method. The second method for preparing cell culture samples for analysis is called the Direct Measure Method. The method of this invention enables the measurement of ion flux through cell membrane ion channels to provide information on ion channel activity. The method described below is directed to the analysis of sodium channels, however, it will be readily appreciated by those skilled in the art that the present invention may be adapted to analyze the activity of other ion channels (e.g. calcium or potassium).

Tracer Ion Method

The lithium ion and rubidium ions are similar to the sodium ion, both in terms of physical and chemical properties such as molecular size and ionic charge. Because of these similarities, these ions are able to pass through many sodium channels, with varying permeability coefficients. An advantage of using lithium or rubidium as tracer ions is that they are not present in biological systems. When the tracer ion concentration of the cell sample is eventually measured after experimental manipulation, the background signal will be very small. In the tracer ion method, ion channels are activated while incubating cell cultures expressing sodium channels with a tracer ion, such as lithium or rubidium, either with or without addition of a compound (i.e. a drug being tested). Due to the similarities between the sodium and lithium and rubidium ions, activated sodium channels will pass the tracer ions. Measurement of the concentration of the tracer ion provides a measure of sodium channel activity. The addition of the compound enables one to identify molecules, which modulate sodium channel activity, hence isolating potential future drug candidates targeting sodium channels. The compound being referred to is the actual drug candidate that the researcher is studying. Due to the low background signal associated with the Tracer Ion Method, the measurement of ion channel activity can be more sensitive than the Direct Measure Method.

Direct Measure Method

In this method the cell cultures are incubated with sodium ions instead of tracer ions. Therefore, when the ion concentration is eventually measured, it will be a direct measurement of sodium ion movement through the sodium channel activity. This method has the advantage that it is more accurate than the tracer ion method because sodium ion movement through the sodium channel is measured directly. The permeability coefficient for sodium is also higher and more biologically relevant to the experimenter.

The direct measure method details a complete protocol for measuring the sodium ion content of cell cultures where cells are incubated with a compound in the presence of sodium ions while sodium channels are activated using an agonist.

The method and procedures below apply equally to the Direct Method and Tracer Method. The only difference is that wherever NaCl is specified to be used in the Direct Measure Method, LiCl or RbCl would be specified to be used in the Tracer Ion Method.

Sample Preparation

Referring to FIG. 1, an outline of the method described below is shown.

a. Tissue Culture

The cells used for the analysis can be from any desired cell line expressing sodium channels and having any other characteristic of interest. This methodology can be used for both voltage-gated or ligand-gated sodium channels. Common cell lines used include Chinese Hamster Ovary, Human Embryonic Kidney or fibroblast cell lines. The cells can either express sodium channels naturally (endogenously) or the sodium channels may be over expressed due to tumorgenic transformations, or they can be expressed as a result of transfection with gene(s) encoding protein(s) of the sodium channel in the appropriate expression vehicle (stable or transient transfection).

The cells to be used are incubated and cultured by traditional means (which are well known to those skilled in the arts). They are then removed from the culture vessel with trypsin solution, and diluted to a final stock concentration of 50,000–200,000 cells/mL 10. Trypsin is a digestive enzyme that is used to dissolve the bonds between cells and the culture vessel and among the cells, thus allowing the cells to be physically removed and manipulated. Cells are then plated out; 200 $\mu$L of the trypsinized cells are seeded into each of the 96 wells of a 12×8 well format microplate. This provides a density of 50,000–100,000 cells/well. The multiwell plate may be biocoated or electrostatic surface treated for cell adherence to the surface. The cells are then allowed to incubate at 37° C. for a typical incubation period of 18 hours 20. The exact incubation period used in an experiment will depend on the desired final cell density, the cell line used, and on the ion channel expression. The purpose of the incubation period is to allow the cells to grow, express ion channels, multiply to increase the cell density in the microplate wells and allow cells to adhere to the surface of the microplate wells.

b. Assay

The cells are washed twice with 200 $\mu$L of a wash medium solution, called Solution A 30. Solution A provides the cells with an isotonic environment and functions to wash the cells before addition of sodium or the tracer ion in Solution B. Solution B contains the agonist, which will depend on the sodium channel studied. The liquid handling steps can be performed manually or automatically by modern robotics. In either case, the washing technique involves the use of a micropipette with a fine tip. The pipette tip must be carefully inserted into the sample well, and carefully draw up the Solution without drawing up any cells or damaging them in the process.

Solution A consists of 135 mM Choline Chloride, 5 mM KCl, 10 mM HEPES, 2 mM $MgCl_2$, 10 mM glucose, 0.2 mM $CaCl_2$. Solution B is the same as Solution A but with the addition of sodium or the tracer ion salt (depending on whether the Direct or the Tracer Ion Method is being used), with agonist. Note that the "agonist" can be a ligand (for ligand-gated ion channels), a solution with positive charge (chemical activation for voltage-gated ion channels), or a modifying agent (example is Veratridine, which removes sodium channel inactivation alone or in the presence of high KCl).

All chemicals and biological substances described and used by this invention are commercially available. HEPES is an acronym for 4-(2-hydroxyethyl)piperazine-i-ethanesulfonic acid. Its chemical formula is $C_8H_{18}N_2O_4S$. Choline is a natural amine that is found in body tissue. In Solution A, the KCl, $MgCl_2$ and $CaCl_2$ mineral salts are required to create a balanced isotonic environment. Glucose is required as a nutritional supplement for the incubating cells. The Solution B contains the Solution A, sodium or the tracer ion salt and an agonist. A compound (i.e. the drug being tested) may be added to the Solution A to determine if there is an effect on sodium channels.

When using this protocol to determine functional compound interaction with sodium channels, 50–200 $\mu$L of the following mixture in Solution B is added; Solution B and compound. The effect of the agonist used in the methodology of this invention is to stimulate sodium channel activity. The entire microplate is incubated at 37° C. for a period of time. This period of time is an experimental factor, and can vary from just a few seconds to 30 minutes 40. After the incubation period, cells are washed three times with 200 $\mu$L of Solution A 50.

Cells are then lysed with 1.5% Triton-X 100 (or 300 mM HCl or 160 mM $HNO_3$) or any other non-ionic detergent 60. Triton-X 100, a common lysing agent, is a non-ionic detergent. It is readily available and sold commercially. Triton-X 100 lyses the cells by solubilizing the lipid bi-layer of the cell membranes. The resulting lysate (the homogenous liquid mixture of dissolved cellular components) is then suitable for immediate analysis, either by FAAS or GFAAS 70.

c. FAAS/GFAAS

Regardless of which method is used to determine the sodium ion channel activity (i.e. the Direct Measure Method or the Tracer Ion Method), there are two different spectroscopic techniques that can be used to actually measure the ion concentration: FAAS or GFAAS. The major difference between the two techniques is that GFAAS is more sensitive than FAAS. When the concentration of ions in the sample is expected to be high, and/or there is a large enough volume of sample, FAAS should be used. Alternatively, when the ion concentration is expected to be very low, and/or there is not much volume of sample to work with, GFAAS would be more appropriate as GFAAS is capable of receiving a smaller sample size than FAAS and has a higher sensitivity than FAAS.

d. Data Processing

The method described here can be used to determine whether a compound (be it a potential cancer drug being tested for sodium channel side effects, or a potential drug specifically designed to target sodium channels) is a blocker of the sodium channel, a non-blocker (no effect), or an opener (inducing channel activation).

For example, if it were found that addition of a compound resulted in a lower concentration of sodium or tracer ions than in the cell sample than without the addition of the compound, then this would indicate that the compound is a blocker of the sodium channels (that is, the compound inhibited the influx of sodium ions into the cells). Alternatively, if it were found that the addition of a compound resulted in a higher concentration of sodium or tracer ions in the cell sample than the sample without the addition of the compound, then this would indicate that the compound is a stimulator of the sodium channel (that is, the compound increased the influx of sodium ions into the cells). If the addition of a compound resulted in no more or no less sodium or tracer ions in the cell sample than in the sample without the addition of the compound, then this would indicate that the compound is a non-blocker of the sodium channel, or neutral (that is, the compound had no effect on the flow of sodium or tracer ions into or out of the cells).
Controls (Table 1)

In most instances where the method of this invention is practiced, controls will also have to be done in order to make the results meaningful. The controls generally follow the method of the invention, with the following differences described below. Generally, for Control #1 through #8, after cells are washed two times in Solution A, 50–200 µL of Solution B is added to the sample wells with and without sodium, and with or without tracer elements with and without compound and with and without agonist. Cells are incubated in Solution B for a set period of time, washed three times in Solution A and lysed as described in FIG. 1. Table 1 is a description of Controls #1 through #8 with contents of Solution B.

Control #1 gives the experimenter information on the concentration of the ions present in the cell before the cells are influenced by the assay. The purpose of Control #2 is to show the activity of the sodium channels in a sodium or tracer ion free medium, with both the compound and agonist present. Here, it is recommended that a standard positive and negative control compound be tested. For example, Lidocaine is known to block sodium channels and would be an ideal negative control compound whereas ω-Agatoxin IV is known to block calcium channels and would be ideal as a positive control compound. This will give the experimenter information on the movement of ions without addition of ions (sodium or tracer) in the presence of a compound which blocks the sodium channels and in the presence of a compound which does not block the sodium channels.

The purpose of Control #3 is to show the activity of the sodium channels in a medium containing sodium or tracer ions, without any influence from agonists or drugs. Control #3 gives the level of basal flux under experimental conditions.

The purpose of Control #4 is to show the activity of the sodium channels in a medium containing sodium or tracer ions, with the agonist present and the compound absent. Control #4 gives the experimenter a window of detection identifying the maximal flux when taken into account with Control #3 (basal flux without agonist).

Control #5 can be done to identify the most adequate environment to detect compounds which activate or open the sodium channels. The compound used will be a positive control, known to activate the ion channel without presence of agonist.

Control #6 determines the movement of ions endogenously present when the sodium channels are activated with an agonist, but with no compound present. The information obtained from this control will help establish the amount of basal level activity that exists in the cell.

The information obtained in Control #7 will identify effects of a compound under the conditions of the assay and can be compared with Control #1 and #6. This control will also determine if the experimental environment affects compound activity (when known compound is used). The analysis of ion movement in Control #8 will determine if the compound is inhibiting ion flow through sodium channels by the addition of a compound known to block sodium channel activity.

TABLE 1

Description of Controls with Contents of Solution B.

| Control # | Sodium or Tracer Ion* | Compound | Agonist** | Information |
|---|---|---|---|---|
| 1 | X | X | X | Ion concentration present in cell line before manipulation. |
| 2 | X | ✓ | ✓ | Movement of ions present without addition of ions. |
| 3 | ✓ | X | X | Movement of added ions, indicating basal flux. |
| 4 | ✓ | X | ✓ | Movement of added ions with channel activation. Combine 3 + 4 for "detection window". |
| 5 | ✓ | ✓ | X | Movement of ions without channel activation can indicate compound which activate sodium channels. |
| 6 | X | X | ✓ | Ion movement in cell line before addition of ions and compound. This information can be combined with Control #3 in determining basal flux. |
| 7 | X | ✓ | X | Identifies compound influence on sodium channel when compared to Control #1 and #6. |
| 8 | ✓ | ✓ | ✓ | Method of screening for sodium channel inhibitors. |

*Addition of sodium or tracer element (lithium or rubidium), depending on which method used, Direct Measure Method or Tracer Ion Method.
**Agonist will depend on the sodium channel studied and can be used for both voltage-gated and ligand-gated ion channels. An agonist (method of channel activation) can be a chemical ligand or modulator or membrane charge stimulus.

What I claim as my invention is:
1. A method of measuring ion flux through a cell membrane sodium ion channel, comprising:
    (a) washing cells expressing said ion channel in a first isotonic solution that does not contain any ions capable of passing through said ion channel, so as to deplete said cells of ions capable of passing through said ion channel;
    (b) removing said first isotonic solution from said cells;
    (c) incubating said cells in a second isotonic solution containing lithium ions;
    (d) washing said cells in said first isotonic solution, so as to create a liquid mixture containing said cells and having an extracellular concentration of said lithium ions that is approximately zero;
    (e) lysing said cells so as to create a homogenous liquid mixture; and
    (f) measuring a concentration of said lithium ions in said homogenous liquid mixture using one of: Flame Atomic Absorption Spectroscopy and Graphite Furnace Atomic Absorption Spectroscopy.

2. The method of claim 1, wherein said second isotonic solution includes an agonist, said agonist operative to activate said ion channel.

3. The method of claim 1, wherein said second isotonic solution includes a compound operative to modulate activity of said ion channel.

4. The method of claim 1, wherein said second isotonic solution includes choline chloride.

5. The method of claim 1, wherein said first isotonic solution includes choline chloride.

6. The method of claim 1, wherein said second isotonic solution includes mineral salts from a group consisting of KCl, MgCl.sub.2, and CaCl.sub.2.

7. The method of claim 1, wherein said first isotonic solution includes mineral salts from a group consisting of KCl, MgCl.sub.2, and CaCl.sub.2.

8. The method of claim 1, wherein said second isotonic solution includes glucose.

9. The method of claim 1, wherein said first isotonic solution includes glucose.

10. The method of claim 1, wherein said second isotonic solution includes 4-(2-hydroxyethyl) piperazine-i-ethanesulfonic acid.

11. The method of claim 1, wherein said first isotonic solution includes 2-hydroxyethyl) piperazine-i-ethanesulfonic acid.

12. The method of claim 1, wherein said cells are lysed using a non-ionic detergent.

* * * * *